(12) United States Patent
Miller et al.

(10) Patent No.: US 9,708,339 B2
(45) Date of Patent: Jul. 18, 2017

(54) 1,3-BENZOTHIAZINONE, SULFOXIDE, AND SULFONE COMPOUNDS WITH ELECTROPHILIC SUBSTITUENT

(71) Applicant: UNIVERSITY OF NOTRE DAME DU LAC, Notre Dame, IN (US)

(72) Inventors: Marvin J. Miller, South Bend, IN (US); Rohit Tiwari, Silver Spring, MD (US)

(73) Assignee: UNIVERSITY OF NOTRE DAME DU LAC, Notre Dame, IN (US)

( * ) Notice: Subject to any disclaimer, the term of this patent is extended or adjusted under 35 U.S.C. 154(b) by 0 days.

(21) Appl. No.: 14/734,657

(22) Filed: Jun. 9, 2015

(65) Prior Publication Data

US 2015/0353572 A1     Dec. 10, 2015

Related U.S. Application Data

(60) Provisional application No. 62/009,687, filed on Jun. 9, 2014.

(51) Int. Cl.
    *C07D 491/113*      (2006.01)
    *C07D 279/08*      (2006.01)

(52) U.S. Cl.
    CPC ........ *C07D 491/113* (2013.01); *C07D 279/08* (2013.01)

(58) Field of Classification Search
    CPC .......................... C07D 491/113; C07D 279/08
    USPC ...................................... 544/6, 50; 514/224.2
    See application file for complete search history.

(56) References Cited

U.S. PATENT DOCUMENTS 8,440,842 B2 *    5/2013    Moellmann .......... C07D 279/08
                                                                         549/14

FOREIGN PATENT DOCUMENTS

FR      WO 2009010163 A1 *   1/2009          C07D 279/08

* cited by examiner

*Primary Examiner* — Kahsay Habte
(74) *Attorney, Agent, or Firm* — Neifeld IP Law, P.C.

(57) ABSTRACT

A compound, having the following formula:

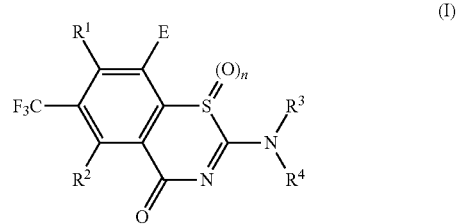

or resonance form thereof, or salt thereof, or salt of resonance form thereof is provided, wherein E includes an electrophilic site, and wherein $R^1$-$R^4$ and n are defined herein. Compositions and methods including the compound are also provided.

20 Claims, 7 Drawing Sheets

9, R = -N(Me)₂, n = 1
10, R = -Ph, n = 1
11, R = -COOEt, n = 0

1,3-BENZOTHIAZINONE, SULFOXIDE, AND SULFONE COMPOUNDS WITH ELECTROPHILIC SUBSTITUENT

RELATED APPLICATIONS

This application claims priority to U.S. Provisional Application No. 62/009,687, filed 9 Jun. 2014, the entire contents of which being hereby incorporated by reference.

STATEMENT REGARDING FEDERALLY FUNDED RESEARCH

This invention was made with government support under grant 2R01AI054193 awarded by the National Institutes of Health (NIH). The government has certain rights in the invention.

FIELD OF THE INVENTION

This application relates to 1,3-benzothiazinone, 1,3-benzothiazinone sulfoxide, and 1,3-benzothiazinone sulfone compounds having an electrophilic substituent, and compositions, methods of making, and their uses. In particular, the application relates to 1,3-benzothiazinone, 1,3-benzothiazinone sulfoxide and 1,3-benzothiazinone sulfone compounds having an azide substituent, compositions containing same, and their use, e.g., as anti-tuberculosis agents.

BACKGROUND

Tuberculosis (TB), is a disease mainly caused by *Mycobacterium tuberculosis* (Mtb). Besides Mtb, other TB-causing mycobacteria include *M. africanum, M. bovis, M. canetti, M. caprae, M. microti, M. mungi* and *M. pinnipedii*. Together these mycobacteria are referred as the *mycobacterium tuberculosis* complex (MTBC).

The complete sequencing of the Mtb genome was completed more than 10 years ago. The last decade has seen major progress in the understanding of TB and, as a result, several therapeutic leads have been identified to help contain the infection. Recently, TMC207 (bedaquiline) was the first new anti-TB agent to be approved in over 40 years. However, TB still remains persistently prevalent, resulting in approximately 2 million deaths every year. The emergence of multi drug resistant (MDR), extensive drug resistant (XDR) and, recently, totally drug resistant strains further emphasizes the desperate, growing need for new anti-TB agents.

The discovery of 1,3-Benzothiazin-4-ones (BTZs), especially BTZ043 (compound 1, FIG. 1) as a potent agent for the treatment of tuberculosis, led subsequently to the identification of several other classes of nitroaromatic compounds as anti-TB agents. BTZ043 and its closest congener PBTZ169 (compound 2, FIG. 1) and analogs have been shown to kill Mtb in vitro, ex vivo, and in mouse models of TB. Both of these agents were shown to be a suicide inhibitor of DprE1, a key enzyme of the cell wall assembly for mycobacteria.

The detailed mode of suicide inhibition of 1 and 2 was elucidated and it was shown to involve the reductive activation of the nitro group into a nitroso intermediate (see FIG. 2A, compound 4) which further covalently inactivates DprE1 (FIG. 2A, compound 5).

BRIEF DESCRIPTION OF THE SEVERAL EMBODIMENTS

The present inventors have designed and synthesized electrophile-substituted 1,3-benzothiazinones and related click chemistry products based on the molecular mode of activation of BTZ043. The inventors have found that 1,3-benzothiazinone azide (BTZ-N3) binds in the essentially same pocket as that of BTZ043, but that, in contrast to BTZ043, the azide analog is an ambident electrophile. The inventors have further found that BTZ-N3 demonstrates impressive activity in vitro against the H37Rv strain of Mtb.

One embodiment provides a compound, having the following formula:

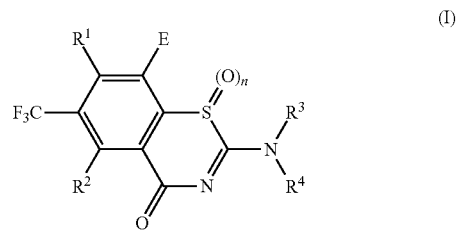

(I)

or resonance form thereof, or salt thereof, or salt of resonance form thereof;

wherein E includes an electrophilic site;

wherein $R^1$-$R^4$ are each independently hydrogen, an alkyl group, a cycloalkyl group, a cycloalkenyl group, a halo group, an alkenyl group, an alkynyl group, an aryl group, a hydroxy group, an acyl group, an oxo group, a mercapto group, an alkylthio group, an alkoxy group, a heterocyclic group, a heteroaryl group, a heteroarylcarbonyl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an alkylsulfonyl group, an arylsulfonyl group, perhaloalkyl group, a perhaloalkoxy group, a perhalocycloalkyl group, a perhaloalkenyl group, a perhaloalkynyl group, a perhaloaryl group, a perhaloaralkyl group, or combination thereof;

wherein $R^3$ and $R^4$ may be taken together with the nitrogen to which they are attached to form a cyclic group;

wherein each group may be optionally and independently straight or branched; wherein each group may be optionally and independently substituted by one or more independent substituents; and wherein one or more than one atom in each group may be optionally and independently replaced with one or more independent heteroatoms;

wherein n is 0, 1, or 2;

and wherein the compound does not have the formulas:

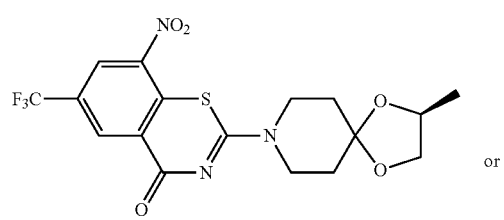

or

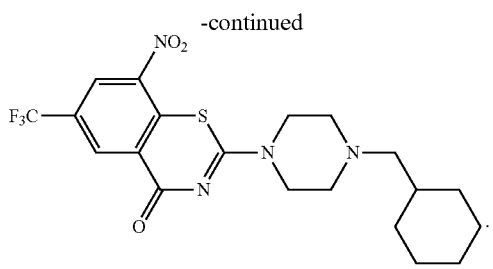

Another embodiment provides a composition, which includes the compound and a physiologically acceptable carrier.

Another embodiment provides a method, which includes administering the compound or the composition to a subject in need thereof, to treat said subject.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from the description.

DESCRIPTION OF THE DRAWINGS

The accompanying drawings form part of the present specification and are included to further demonstrate certain embodiments, which are not intended to be limiting, of the present invention. The invention may be better understood by reference to one or more of these drawings in combination with the description of the several embodiments presented herein.

DETAILED DESCRIPTION OF THE SEVERAL EMBODIMENTS

Figure 2:
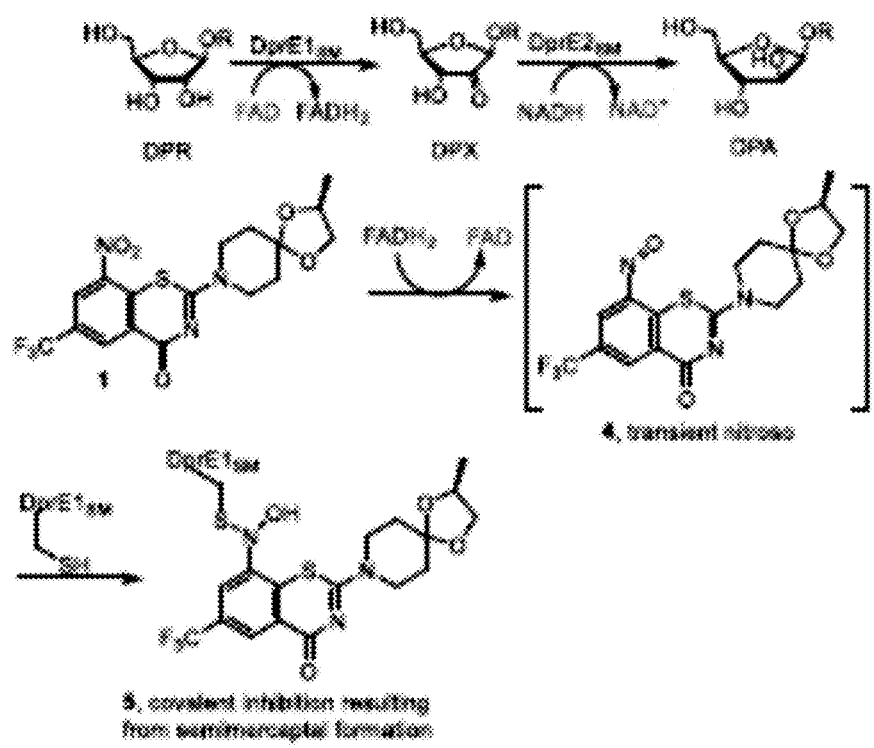
FIG. 2. DprE1 enzyme inhibition by BTZ043 and PBTZ169 and cine chemistry.
Figure 2:
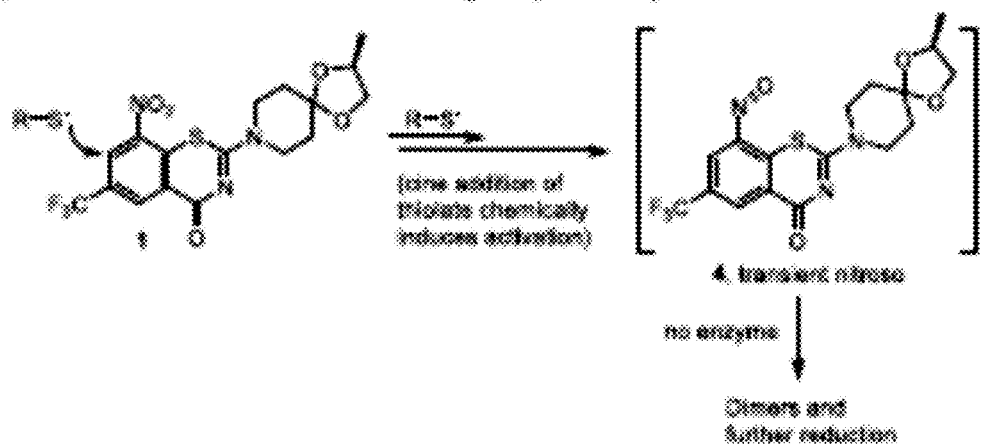

The present inventors' efforts in the mechanistic understanding of the reductive activation of 1 suggest that 1 and other related nitroaromatic anti-TB agents may undergo chemical activation of its nitro group to the nitroso intermediate by a cine addition reactions with either nucleophilic thiolates or hydrides (FIG. 2B). Therefore cine addition of either thiolate from the essential cysteine of DprE1 or hydride from a cofactor FADH2 may be responsible for the generation of the nitroso intermediate at the enzyme active site. It should be noted that in the absence of the enzyme, such nitroso intermediates undergo dimerization or subsequent reduction(s) to hydroxylamines and amines.

Figure 1:
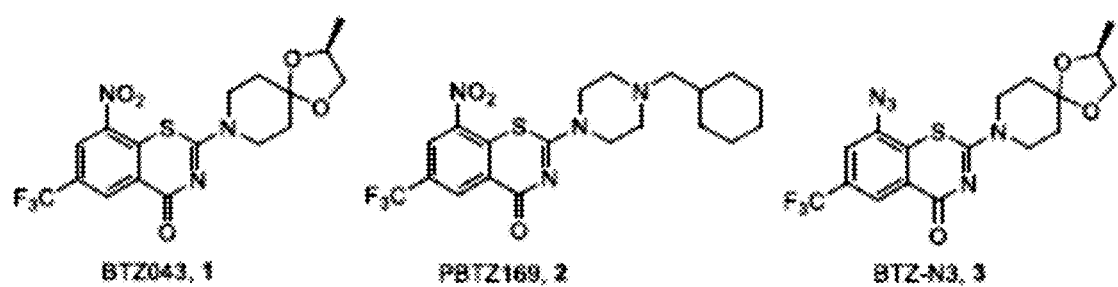
FIG. 1. Shows structures of 1,3-benzothiazinone anti-TB agents, BTZ043, PBTZ169 and BTZ-N3.

The inventors envisioned that the substitution of the nitro group of 1 by an azide (compound 3, FIG. 1) could result in the similar mode of activation and/or inhibition since the first nucleophilic step of a cine addition by either thiolate from the essential cysteine or hydride from FADH$_2$ would be mechanistically reasonable. However, in the case of azide group the formation of the nitroso derived "semimercaptal adduct" would not be possible and activity might depend on subsequent possible chemistry. Recent studies identified "non-nitroaromatic" hits that bind to the same pocket as BTZ043 without formation of the covalent semimercaptal adduct. Therefore, the inventors synthesized and evaluated the anti-TB activity of 3.

Figure 3:
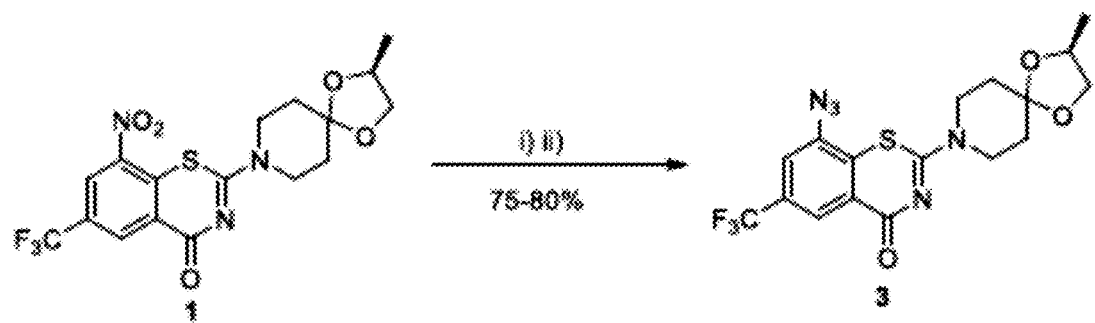
FIG. 3. Synthesis of BTZ-N3. Reagent and conditions: i) Fe, CH3COOH, 120° C. ii) t-BuONO, TMSN$_3$ FIG. 4. Overlay of the docked poses of 3 and 4. The carbons of 4 are colored in cyan whereas carbons of 3 are in white.

Compound 3 was synthesized in two steps from 1 by reducing the nitro group of the latter using Fe/CH$_3$COOH under reflux conditions (120° C.) for 2 h to afford the reduced amine 6. The amino group of 6 was subsequently treated with tert-butyl nitrite (t-BuONO) followed by azidotrimethylsilane (TMSN$_3$) to afford 3 in 70% yield over two steps (FIG. 3).

Figure 4:
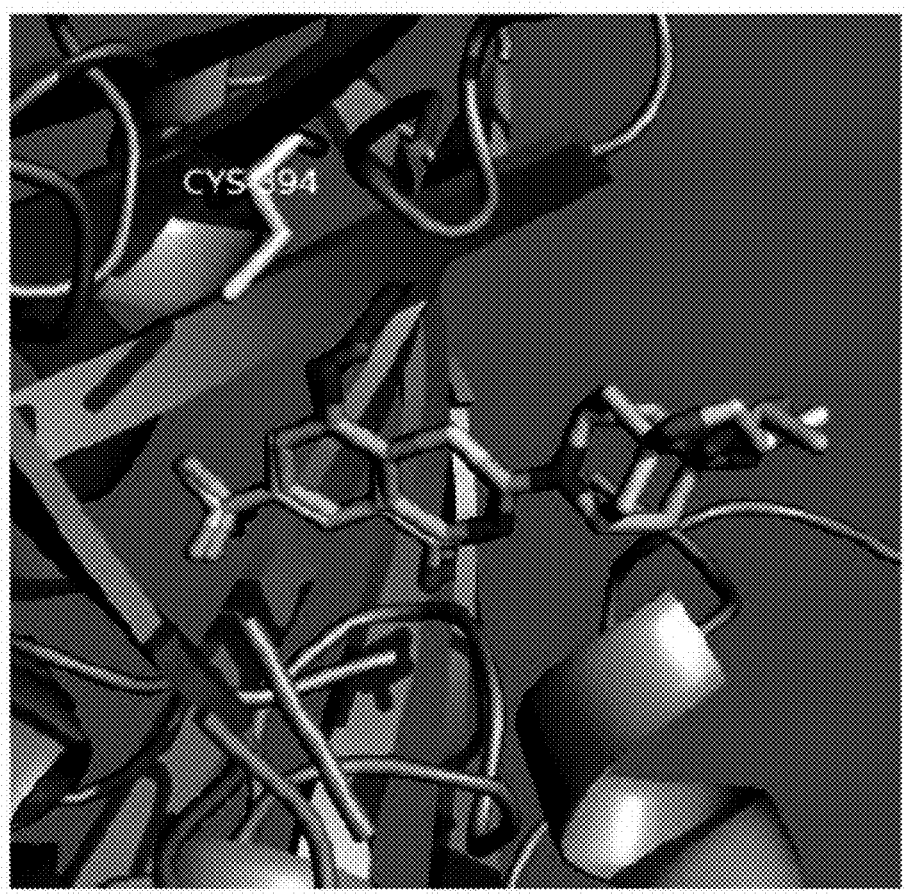

In order to explore and compare the binding of 3 with that of 1 at the active site of DprE1, both 3 and 1 were docked into the crystal structure of DprE1 (PDB #4F4Q) using Glide. Since compound 1 was crystallized as a covalent adduct with DprE1, the optimization of the docking protocol was achieved as previously described. Briefly, the benzothiazinone ligand (semimercaptal) present in the crystal structure was modeled by docking its nitroso intermediate (compound 4). Docking of compound 4 into DprE1 mimicked the binding pattern of the benzothiazinone (semimercaptal) intermediate (see FIG. 4).

Next, the docking was repeated with BTZ-N3 to explore its binding. The docking study indicated that it binds essentially in the same binding pocket as that of 5. This docking provided further incentive to evaluate 3 in anti-TB assays.

The in vitro activity of compound 3 in two different mycobacterial growth media (7H12 and GAS) is summarized in Table 1. The corresponding activity of 1 is also shown in Table 1 for comparison.

TABLE 1

In vitro activity azide 3, amine 6, desazido BTZ, 8 (FIG. 6) and click chemistry products 9-11 (FIG. 7) and controls against H37Rv strain of Mtb (in 7H12 and GAS media).

| Compounds | MABA:MIC 7H12 (μM) | MABA:MIC GAS(μM) |
| --- | --- | --- |
| 3 | 0.47 | 0.46 |
| 6 | >1 (87%) | >1 (0%) |
| 8 | >1 (87%) | >1 (36%) |
| 9 | 0.87 | 0.95 |
| 10 | >1 (0%) | >1 (0%) |
| 11 | 0.93 | >1 (34%) |
| BTZ043 | <0.004 | <0.004 |
| INH | 0.1 | 0.03 |
| Rifampin | 0.05 | 0.04 |

Table 1: Comps, Compounds; MABA, microplate alamar blue assay; GAS, glycerol-alanine-salts medium; 7H12, 7H9 medium plus casitone, palmitic acid, albumin and catalase.

As can be seen from Table 1, compound 3 showed outstanding activity against the H37Rv strain of Mtb albeit not as high as the parent BTZ043 itself. The activity of 3 was comparable to that of standard front line drugs, INH and rifampin against Mtb.

Similar to earlier studies of the mechanistic chemistry of BTZ043, and because of the similarity in electronic features to that of 1, the possible cine reactivity of azide 3 with nucleophiles was investigated. Mulliken charges calculated by semiempirical AM1 method (see Table 2) indicated that, in contrast to BTZ043, azide 3 has two highly electrophilic sites namely "the cine position (see Table 2, C1)" and the terminal nitrogen of the azide group (see Table 2, N3).

TABLE 2

Calculated Mulliken charges for compounds 1, 3, and 9.

[Structure of BTZ043 labeled as compound 1, showing $NO_2$, Cl, $F_3C$ substituents on benzothiazinone with spiro ketal piperidine]

[Structure of BTZ-N3 labeled as compound 3, showing $N_3$ (with N1, N2, N3 labels), Cl, $F_3C$ substituents on benzothiazinone with spiro ketal piperidine]

[Structure of compound 9, showing dimethylaminomethyl-triazole (with N1, N2, N3 labels), Cl, $F_3C$ substituents on benzothiazinone with spiro ketal piperidine]

| Mulliken Charges | 1 | 3 | 9 |
|---|---|---|---|
| C1 | 0.21 | 0.14 | 0.09 |
| N1 | 0.57 | >0.23 | >0.14 |
| N2 | NA | 0.22 | 0.01 |
| N3 | NA | >0.01 | >0.05 |

Table 2: The Mulliken charges are shown only for the numbered atoms for comparison purposes.

Figure 5:
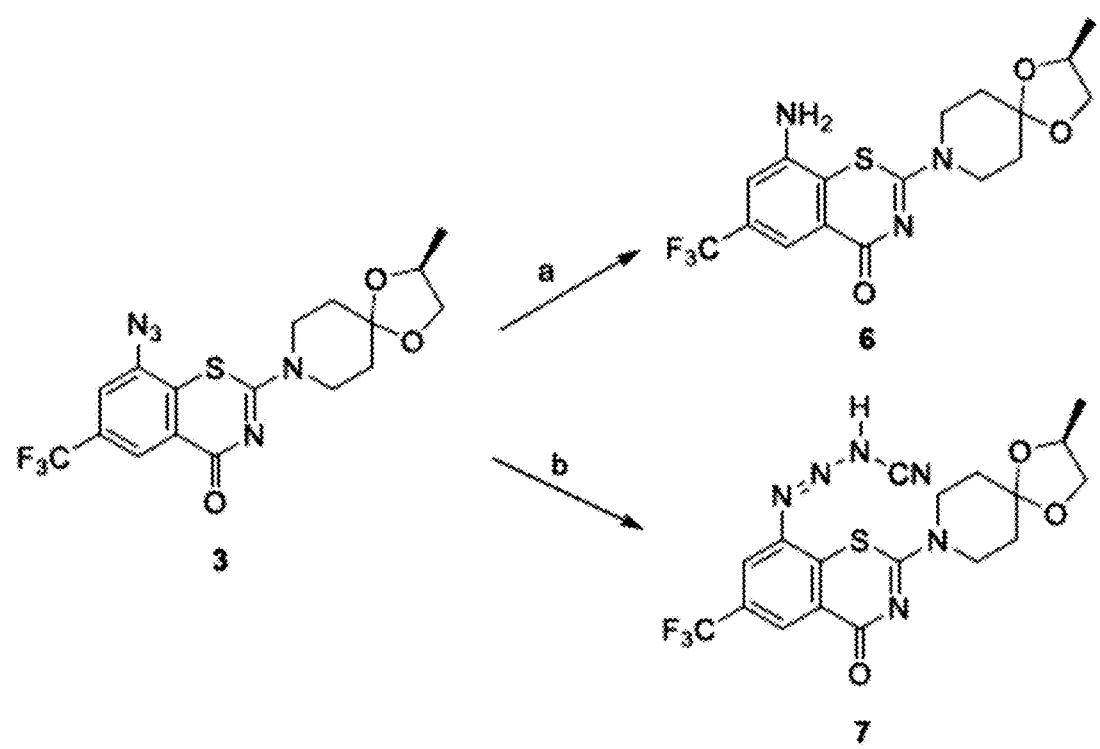
FIG. 5. Shows reactivity of BTZ-N3 with thiolates and cyanides. Reagent and conditions: i) NaSMe, CH$_3$CN/H$_2$O ii) KCN, CH$_3$CN/H$_2$O.

To probe further, 3 was reacted with sodium methanethiolate (NaSMe) and potassium cyanide (KCN) in acetonitrile/water (FIG. 5). Interestingly, the reaction of 3 with NaSMe did result in rapid net reduction of the azide to an amine. Although mechanistic details have not yet been elucidated, the reactivity is consistent with its anti-TB activity.

The inventors considered that earlier studies of the reaction of BTZ043 with other nucleophiles, including cyanide were also consistent with cine addition chemistry. However, while reaction of azide 3 with cyanide was clean and facile, the product obtained (cyanotriazene, 7) resulted from nucleophilic addition at the terminal nitrogen of the azide. This indicates that, although compound 3 has a benzothiazinone scaffold, it might, however, undergo a somewhat different reaction (mode of activation) at the active site of DprE1.

Figure 6:
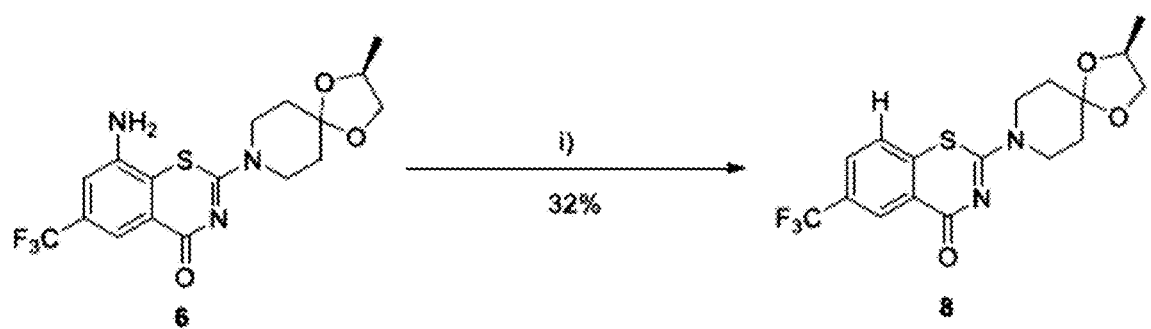
FIG. 6. Synthesis of "desazido-BTZ-N3." Reagent and conditions: i) t-BuONO, THF, 30 min.
Figure 7:
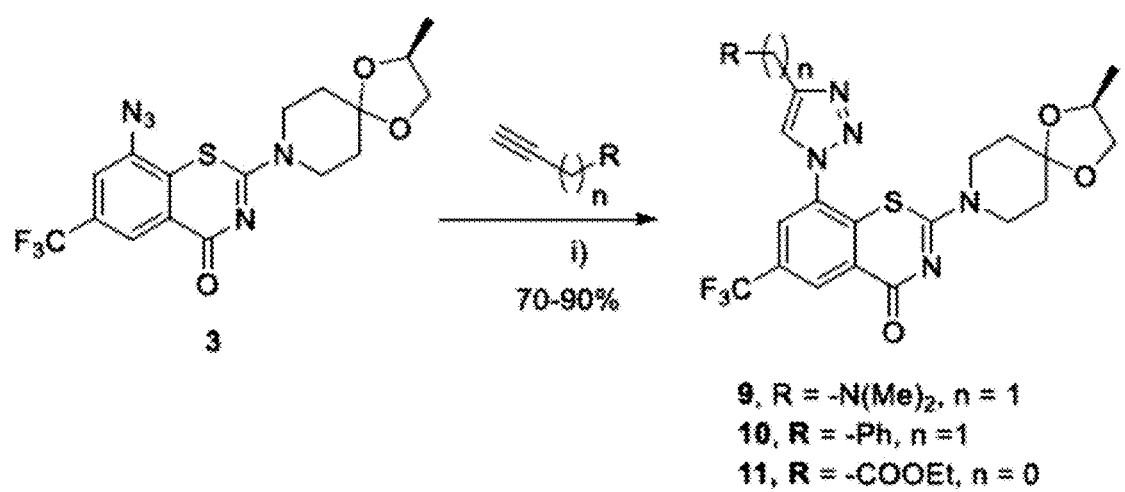
FIG. 7. Click Reaction of BTZ-N3. Reagent and conditions: i) CuSO$_4$ 5H$_2$O, Sodium ascorbate, tert-butanol/water.

To substantiate that the observed anti-TB activity of the BTZ-N3 was mainly because of the combination of both the azide functionality (as a key requirement) and benzothiazinone scaffold, the corresponding "desazido-BTZ-N3" (compound 8) was synthesized as a control molecule (FIG. 6). As shown in FIG. 6, compound 6 was treated with tert-butyl nitrite in THF for a period of 30 min, which afforded 8 in 55% yield after purification. However, unlike its predecessors BTZ-N3 or BTZ043, compound 8 was not significantly active against H37Rv strain of Mtb.

The availability of benzothiazinone azide 3 afforded an opportunity to synthesize and evaluate some representative Click chemistry reaction products. Therefore, compound 3 was treated with N,N-dimethylpropargylamine, phenylpropyne and ethylpropiolate as representative alkynes under standard reaction conditions (FIG. 7) to obtain compounds 9, 10 and 11 respectively in 70-90% yields.

The decrease in the electron withdrawing ability of the benzothiazinone ring (as opposed to BTZ-N3 and BTZ043) brought about by the triazole functionality was determined by Mulliken charge calculations (Table 1) and became further evident by their drastically reduced anti-mycobacterial activity (Table 2). Additionally a docking study carried out with 9 as a representative of this class of compounds indicated that the whole scaffold is positioned further away from the binding pocket.

By comparison of the anti-TB activities of 3, 6 and 8-11, it is clear that only azide 3 has impressive activity against TB. The reduced of activity of amine 8 and trizole Click products 9-11 again emphasize that a suitable electronically activating functional group (e.g., —$NO_2$, or —$N_3$) is necessary for anti-TB activity of the 1,3-benzothiazinones. The biological activity of BTZ-N3 combined with the chemical reactivity described in FIG. 5 indicates that BTZ-N3 might have alternative modes of reactivity with DprE1. The studies described here indicate that the BTZ scaffold may provide still further opportunities for development of much needed new anti-TB agents.

In some embodiments, the form of the compound (I) is not particularly limiting. For example, it may be in a resonance form, a salt form, or salt of resonance form. Mixtures of different forms, and compositions that include mixtures of forms are possible.

In some embodiments, compound (I) is in the salt form.
In some embodiments, compound (I) is in a resonance form.
In some embodiments, the resonance form is an ionic resonance form.

So long as it includes an electrophilic site, E is not particularly limiting. Non-limiting examples of E include —$N_3$, —$NO_2$, —NO, —$NR_3^+$ (wherein each R is independently H, alkyl, aryl, or any combination thereof), —C(=O)R (wherein R is independently H, alkyl, aryl, hydroxyl, alkoxy, phenoxy, —$NH_2$), —$CX_3$ (wherein X=F, Cl, Br, I), —CN, or —$SO_3H$ In some embodiments, the electrophilic site is a terminal nitrogen atom of an azide.
In some embodiments, E is —$N_3$ or —$NO_2$.
In some embodiments, E is —$N_3$.

In some embodiments, each $R^1$-$R^5$ group may independently and optionally be selected from one or more of the substituent groups described herein. In some embodiments, each $R^1$-$R^5$ group may independently and optionally be further substituted, and each $R^1$-$R^5$ group may independently and optionally connected directly to the relevant parent structure via one or more chemical bonds, or may be independently and optionally connected indirectly to the relevant parent structure via one or more divalent intervening substituent groups.

In some embodiments, $R^1$-$R^5$ are each independently hydrogen, an alkyl group, a cycloalkyl group, a cycloalkenyl group, a halo group, an alkenyl group, an alkynyl group, an aryl group, a hydroxy group, an acyl group, an oxo group, a mercapto group, an alkylthio group, an alkoxy group, a heterocyclic group, a heteroaryl group, a heteroarylcarbonyl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an alkylsulfonyl group, an arylsulfonyl group, perhaloalkyl group, a perhaloalkoxy group, a perhalocycloalkyl group, a perhaloalkenyl group, a perhaloalkynyl group, a perhaloaryl group, a perhaloaralkyl group, oxidized form thereof, or combination thereof.

In some embodiments, each $R^1$-$R^5$ group may independently and optionally be selected from one or more of hydrogen, an alkyl group, a cycloalkyl group, a cycloalkenyl group, a halo group, an alkenyl group, an alkynyl group, an aryl group, a hydroxy group, an acyl group, an oxo group, a mercapto group, an alkylthio group, an alkoxy group, a heterocyclic group, a heteroaryl group, a heteroarylcarbonyl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an alkylsulfonyl group, an arylsulfonyl group, oxidized form thereof, or combination thereof.

In some embodiments, each $R^1$-$R^5$ group may independently and optionally be selected from one or more of hydrogen, an alkyl group, a cycloalkyl group, a cycloalkenyl group, a halo group, an alkenyl group, an alkynyl group, an aryl group, a hydroxy group, an acyl group, an alkoxy group, a heterocyclic group, a heteroaryl group, a heteroarylcarbonyl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, oxidized form thereof, or combination thereof.

In some embodiments, each $R^1$-$R^5$ group may independently and optionally be selected from one or more of hydrogen, an alkyl group, an alkenyl group, an alkynyl group, an aryl group, an acyl group, an alkoxy group, a heterocyclic group, a heteroaryl group, a heteroarylcarbonyl group, an aryloxy group, a heteroaryloxy group, an aralkyl group, a heteroaralkyl group, an aralkoxy group, a heteroaralkoxy group, a carbamoyl group, an alkylcarbonyl group, an alkoxycarbonyl group, an alkylaminocarbonyl group, a dialkylamino carbonyl group, an arylcarbonyl group, an aryloxycarbonyl group, oxidized form thereof, or combination thereof.

In some embodiments, each $R^1$-$R^5$ group may independently and optionally be selected from one or more of hydrogen, an alkyl group, a cycloalkyl group, a cycloalkenyl group, an alkenyl group, an alkynyl group, an aryl group, a heterocyclic group, a heteroaryl group, an aralkyl group, a heteroaralkyl group, oxidized form thereof, or combination thereof.

In some embodiments, $R^1$-$R^5$ are each independently hydrogen, alkyl, substituted alkyl, linear alkyl, branched alkyl, allyl, substituted allyl, heteroalkyl, cycloalkyl, aryl, substituted aryl, heteroaryl, acyl, aroyl, heteroaroyl, or combination thereof.

In some embodiments, $R^1$-$R^5$ are each independently hydrogen, alkyl, substituted alkyl allyl, substituted allyl, heteroatom substituted alkyl, cycloakyl, aryl, substituted aryl, heteratom substituted aryl, heteroaryl, acyl, aroyl, heteroaroyl, or combination thereof.

In some embodiments, $R^1$-$R^5$ are each independently hydrogen, alkyl, allyl, cycloalkyl, aryl, acyl, aroyl, or combination thereof.

In some embodiments, each $R^1$-$R^5$ group may independently and optionally be substituted, unsubstituted, saturated, unsaturated, or combination thereof.

In some embodiments, one or more than one atom in one or more of $R^1$-$R^5$ is independently replaced with one or more independent heteroatom, oxidized form thereof, or combination thereof.

In some embodiments, each $R^1$-$R^5$ group may independently and optionally have one or more atoms replaced with one or more heteroatoms, e.g., N, O, P, S, oxidized form thereof, or combination thereof.

In some embodiments, one or more than one carbon in one or more of $R^1$-$R^5$ is independently replaced with one or more independent heteroatom selected from the group consisting of N, O, S, or combination thereof.

In some embodiments, $R^1$-$R^4$ are each independently hydrogen, an alkyl group, a cycloalkyl group, a cycloalkenyl group, a halo group, an alkenyl group, an alkynyl group, an aryl group, a hydroxy group, an oxo group, a mercapto group, an alkylthio group, an alkoxy group, a heterocyclic group, a heteroaryl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an alkylsulfonyl group, an arylsulfonyl group, perhaloalkyl group, a perhaloalkoxy group, a perhalocycloalkyl group, a perhaloalkenyl group, a perhaloalkynyl group, a perhaloaryl group, a perhaloaralkyl group, or combination thereof.

In some embodiments, $R^3$ and $R^4$ may be taken together with the nitrogen to which they are attached to form a cyclic group.

In some embodiments, $R^3$ and $R^4$ do not form a cyclic group.

In some embodiments, wherein when the $R^3$ and $R^4$ groups are taken together with the nitrogen to form a cyclic group, the cyclic group may be suitably derived from a divalent cycloalkylene group or divalent heterocycloalkylene group. Combinations of cycloalkylene and heterocycloalkylene groups are contemplated herein. The divalent cycloalkylene and heterocycloalkylene groups may be suitably derived from the respective cycloalkyl or heterocyclic groups.

In some embodiments, the cyclic group formed from the $R^3$ and $R^4$ groups taken together with the nitrogen is an aryl group, heteroaryl group, or combination thereof. The aryl and heteroaryl group may be suitably derived from a divalent arylene group or divalent heteroarylene group. The divalent arylene and heteroarylene groups may be suitably derived from the respective aryl or heteroaryl groups.

In some embodiments, the $R^3$ and $R^4$ cyclic group includes a 3, 4, 5, 6 membered ring or larger, which contains one or more of carbons, substituted carbons and/or heteroatoms (N, O, S) in addition to their oxidized versions, including alkenes and cycloalkenes, heterocycles and mixed carbocycle and heterocyclic moieties.

In some embodiments, $R^3$ and $R^4$ taken together with the nitrogen to which they are attached form a $C_3$-$C_{10}$ cyclic group.

In some embodiments, $R^3$ and $R^4$ taken together with the nitrogen to which they are attached form a $C_3$-$C_6$ cyclic group.

In some embodiments, $R^3$ and $R^4$ taken together with the nitrogen to which they are attached form a cycloalkene, heterocycle, mixed carbocycle and heterocycle, oxidized form thereof, or combination thereof.

In some embodiments, wherein $R^3$ and $R^4$ taken together with the nitrogen to which they are attached form a cyclic group, one or more than one carbon in the cyclic group is independently and optionally replaced with one or more heteroatom or oxidized form thereof.

In some embodiments, the group:

wherein $R^3$ and $R^4$ are taken together to form a cyclic group, may have the following cyclic structure (II):

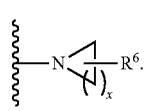

(II)

The x in the cyclic structure (II) is not particularly limiting and may have any value. In some embodiments, x is 1-10. This range includes all values and subranges therebetween, including 1, 2, 3, 4, 5, 6, 7, 8, 9, and 10.

So long as the nitrogen is present, the remaining ring portion of the cyclic structure (II) is not particularly limiting. The remaining ring portion may be suitably derived from a divalent cycloalkylene group, divalent heterocycloalkylene group, divalent arylene group, divalent heteroarylene group, one or more of the divalent intervening substituent groups, oxidized form thereof, or combination thereof. The cyclic structure (II) may have one or more than one ring. Combinations of different are possible.

In the cyclic structure (II), one or more than one of the ring atoms may be optionally and independently replaced with one or more heteroatoms, e.g., N, O, P, S, oxidized form thereof, or combination thereof.

In the cyclic structure (II), one or more than one of the ring atoms may be optionally and independently substituted with one or more $R^6$ groups. If more than one $R^6$ group is present, they may be the same or different.

In some embodiments, each $R^6$ group may independently and optionally be selected from one or more of the substituent groups described herein.

In some embodiments, each $R^6$ group may independently and optionally be selected from one or more of hydrogen, an alkyl group, a cycloalkyl group, a cycloalkenyl group, a halo group, an alkenyl group, an alkynyl group, an aryl group, a hydroxy group, an acyl group, an oxo group, a mercapto group, an alkylthio group, an alkoxy group, a heterocyclic group, a heteroaryl group, a heteroarylcarbonyl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an alkylsulfonyl group, an arylsulfonyl group, oxidized form thereof, or combination thereof.

In some embodiments, each $R^6$ group may independently and optionally be selected from one or more of hydrogen, an alkyl group, a cycloalkyl group, a cycloalkenyl group, a halo group, an alkenyl group, an alkynyl group, an aryl group, a hydroxy group, an acyl group, an alkoxy group, a heterocyclic group, a heteroaryl group, a heteroarylcarbonyl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, oxidized form thereof, or combination thereof.

In some embodiments, each $R^6$ group may independently and optionally be selected from one or more of hydrogen, an alkyl group, a cycloalkyl group, a cycloalkenyl group, an alkenyl group, an alkynyl group, an aryl group, an acyl group, an alkoxy group, a heterocyclic group, a heteroaryl group, a heteroarylcarbonyl group, an aryloxy group, a heteroaryloxy group, an aralkyl group, a heteroaralkyl group, an aralkoxy group, a heteroaralkoxy group, a carbamoyl group, an alkylcarbonyl group, an alkoxycarbonyl group, an alkylaminocarbonyl group, a dialkylamino carbonyl group, an arylcarbonyl group, an aryloxycarbonyl group, oxidized form thereof, or combination thereof.

In some embodiments, each $R^6$ group may independently and optionally be selected from one or more of hydrogen, an alkyl group, a cycloalkyl group, a cycloalkenyl group, an alkenyl group, an alkynyl group, an aryl group, a heterocyclic group, a heteroaryl group, an aralkyl group, a heteroaralkyl group, oxidized form thereof, or combination thereof.

Each $R^6$ group may independently and optionally be further substituted, and each $R^6$ group may independently and optionally connected directly to the relevant parent structure via one or more chemical bonds, or may be independently and optionally connected indirectly to the relevant parent structure via one or more divalent intervening substituent groups.

In some embodiments, $R^1$-$R^6$ are each independently an alkyl or alkenyl group. In some embodiments, the alkenyl group is an allyl group. In some embodiments, the allyl group may be linear, branched, substituted, unsubstituted, or combination thereof.

In some embodiments, the cycloalkyl may be substituted or unsubstituted, and the alkyl portion of which may be linear, branched, substituted, unsubstituted, or combination thereof.

In some embodiments, the aryl, acyl, and aroyl may be independently substituted or unsubstituted.

In some embodiments, the compound (I) has one of the following formulas:

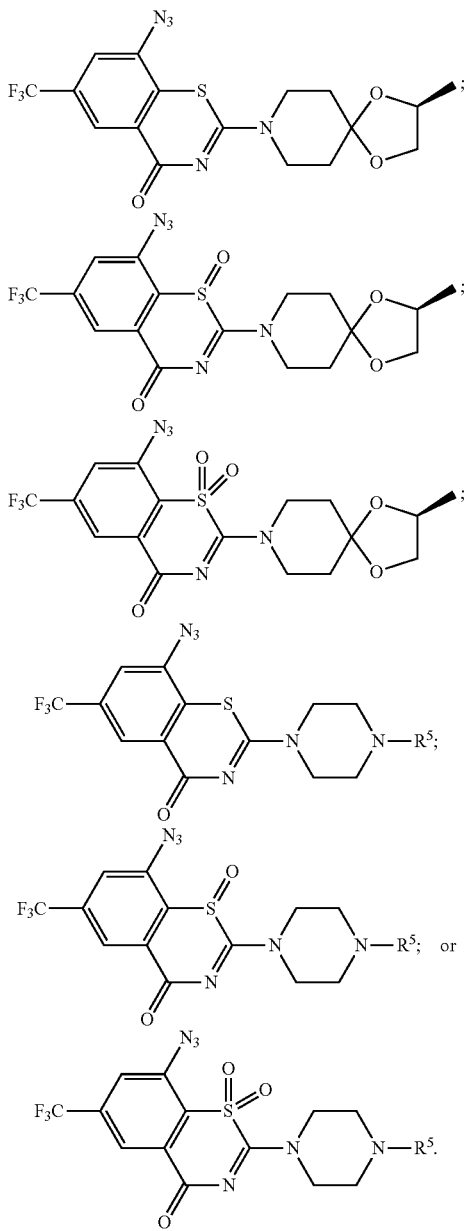

In some embodiments, $R^5$ is defined hereinabove.

In some embodiments, $R^5$ is hydrogen, an alkyl group, a cycloalkyl group, a cycloalkenyl group, a halo group, an alkenyl group, an alkynyl group, an aryl group, a hydroxy group, an acyl group, an oxo group, a mercapto group, an alkylthio group, an alkoxy group, a heterocyclic group, a heteroaryl group, a heteroarylcarbonyl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an alkylsulfonyl group, an arylsulfonyl group, perhaloalkyl group, a perhaloalkoxy group, a perhalocycloalkyl group, a perhaloalkenyl group, a perhaloalkynyl group, a perhaloaryl group, a perhaloaralkyl group, oxidized form thereof, or combination thereof.

In some embodiments, $R^5$ is hydrogen, an alkyl group, a cycloalkyl group, a cycloalkenyl group, a halo group, an alkenyl group, an alkynyl group, an aryl group, a hydroxy group, an oxo group, a mercapto group, an alkylthio group, an alkoxy group, a heterocyclic group, a heteroaryl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an alkylsulfonyl group, an arylsulfonyl group, perhaloalkyl group, a perhaloalkoxy group, a perhalocycloalkyl group, a perhaloalkenyl group, a perhaloalkynyl group, a perhaloaryl group, a perhaloaralkyl group, or combination thereof.

In some embodiments, a composition is provided, which includes the compound (I) and a physiologically acceptable carrier.

In some embodiments, a method is provided, which includes administering the compound or the composition to a subject in need thereof, to treat the subject.

In some embodiments, the subject is known or suspected to need treatment for one or more maladies related to non-pathogenic mycobacterial strain, *M. smegmatis, M. vaccae, M. aurum,* or combination thereof.

In some embodiments, the subject is known or suspected to need treatment for one or more maladies related to Gram positive bacteria, *S. aureus, M. luteus*, or combination thereof.

In some embodiments, the subject is known or suspected to need treatment for one or more maladies related to Gram negative bacteria, *P. aeruginosa, A. baumanii*, or combination thereof.

In some embodiments, the subject is known or suspected to need treatment for one or more maladies related to pathogenic mycobacterial strain, *M. tuberculosis, M. bovis, M. marinum, M. kansasaii*, H37Rv, *M. africanum, M. canetti, M. caprae, M. microti, M. mungi, M. pinnipedii,* myobacterium tuberculosis complex, tuberculosis, or combination thereof.

In some embodiments, the subject is known or suspected to need treatment for one or more maladies related to non-pathogenic mycobacterial strain, *M. smegmatis, M. vaccae, M. aurum,* Gram positive bacteria, *S. aureus, M. luteus,* Gram negative bacteria, *P. aeruginosa, A. baumanii,* pathogenic mycobacterial strain, *M. tuberculosis, M. bovis, M. marinum, M. kansasaii,* H37Rv, *M. africanum, M. canetti, M. caprae, M. microti, M. mungi, M. pinnipedii,* myobacterium tuberculosis complex, tuberculosis, or combination thereof.

In some embodiments, e.g., in the case of TB, the compound may be administered to a subject in need thereof together with or in addition to one or more of Isoniazid, Rifampin, Rifadin, Rimactane, Ethambutol, Myambutol, Pyrazinamide, antibiotic, fluoroquinolone, Amikacin, Kanamycin, Capreomycin, Bedaquiline, Delamanid, PA-824, Linezolid, Sutezolid, or any combination thereof.

In some embodiments, the subject is mammalian, human, livestock, cow, pig, horse, or the like.

In some embodiments, a method is provided, which includes killing or inhibiting the growth of a population of one or more of non-pathogenic mycobacterial strain, *M. smegmatis, M. vaccae, M. aurum*, Gram positive bacteria, *S. aureus, M. luteus*, Gram negative bacteria, *P. aeruginosa, A. baumanii*, pathogenic mycobacterial strain, *M. tuberculosis, M. bovis, M. marinum, M. kansasaii*, H37Rv, *M. africanum, M. canetti, M. caprae, M. microti, M. mungi, M. pinnipedii*, myobacterium tuberculosis complex, tuberculosis, or combination thereof, by contacting one or more member of said population with the compound or composition.

In some embodiments, the population is present on a surface, and the compound or composition is contacted with said surface.

In some embodiments, an alkyl group is a univalent, acyclic, straight or branched, substituted or unsubstituted, saturated or unsaturated, hydrocarbon radical. In some embodiments, the alkyl group has the general formula (notwithstanding optional unsaturation, substitution or the like) —$C_nH_{2n+1}$. In some embodiments, n is 1-20 (($C_1$-$C_{20}$) alkyl), which may suitably include $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ alkyl groups. In some embodiments, the alkyl group may be straight or branched, substituted or unsubstituted, saturated or unsaturated, or any combination thereof. In some embodiments, one or more hydrogens may be optionally and independently replaced by one or more substituent groups. In some embodiments, one or more carbon atoms may be optionally and independently replaced with one or more heteroatoms such as O, S, N, B, or any combination thereof. In some embodiments, the alkyl group may contain one or more double bond, one or more triple bond, or any combination thereof. In some embodiments, the alkyl group is attached to the parent structure through one or more independent divalent intervening substituent groups. Some examples of alkyl groups, which are not intended to be limiting, include methyl, ethyl, n-propyl, isopropyl, n-butyl, iso-butyl, secondary-butyl, tertiary-butyl, and the like.

In some embodiments, a cycloalkyl group is a univalent, mono- or polycyclic, substituted or unsubstituted, saturated or unsaturated hydrocarbon radical. In some embodiments, the cycloalkyl group has the general formula (notwithstanding optional unsaturation, substitution, or the like) —$C_nH_{2n-1}$. In some embodiments, n is 3-20 (($C_3$-$C_{20}$) cycloalkyl), which may suitably include $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ cycloalkyl groups. In some embodiments, the cycloalkyl group is substituted or unsubstituted, saturated or unsaturated, mono-, bi-, tri-, or poly-cyclic, or any combination thereof. In some embodiments, one or more hydrogens may be optionally and independently replaced by one or more substituent groups. In some embodiments, the cycloalkyl group may have one or more sites of unsaturation, e.g., it may contain one or more double bond, one or more triple bond, or any combination thereof to form a cycloalkenyl or cycloalkynyl group, or combination thereof. In some embodiments, one or more carbon atoms may be optionally and independently replaced with one or more heteroatoms such as O, S, N, B, or any combination thereof. In some embodiments, the cycloalkyl group is attached to the parent structure through one or more independent divalent intervening substituent groups. Some examples of cycloalkyl groups, which are not intended to be limiting, include cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, and the like. In the case of polycyclic groups, one or more of the rings may be tethered together via bond or other divalent intervening substituent group, fused (e.g., in which one or more rings shares two or more carbon atoms or heteroatoms, joined via a single atom (e.g., spiro compound), or bridged.

In some embodiments, an alkenyl group is a univalent, straight or branched, substituted or unsubstituted, unsaturated hydrocarbon radical. In some embodiments, the alkenyl group has the general formula (notwithstanding optional substitution, higher degree of unsaturation, or the like) —$C_nH_{2n-2}$. In some embodiments, n is 2-20 (($C_2$-$C_{20}$) alkenyl), which may suitably include $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ alkenyl groups. In some embodiments, the alkenyl group may be straight or branched, substituted or unsubstituted, have more than one degree of unsaturation, or any combination thereof. In some embodiments, one or more carbon atoms may be optionally and independently replaced with one or more heteroatoms such as O, S, N, B, or any combination thereof. In some embodiments, the alkenyl group is attached to the parent structure through one or more independent divalent intervening substituent groups. Some examples of alkenyl groups, which are not intended to be limiting, include ethenyl, 1-propenyl, 2-propenyl (allyl), iso-propenyl, 2-methyl-1-propenyl, 1-butenyl, 2-butenyl, alkadienes, alkatrienes, and the like.

In some embodiments, an alkynyl group is a univalent, straight or branched, substituted or unsubstituted, hydrocarbon radical that contains one or more carbon-carbon triple bond. In some embodiments, the alkenyl group has the general formula (notwithstanding optional substitution, higher degree of unsaturation, or the like) —$C_nH_{2n-3}$. In some embodiments, n is 2-20 (($C_2$-$C_{20}$) alkynyl), which may suitably include $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ alkynyl groups. In some embodiments, the alkynyl group may be straight or branched, substituted or unsubstituted, have more than one degree of unsaturation, or any combination thereof. In some embodiments, one or more carbon atoms may be optionally and independently replaced with one or more heteroatoms such as O, S, N, B, or any combination thereof. In some embodiments, the alkynyl group is attached to the parent structure through one or more independent divalent intervening substituent groups. Some examples of alkynyl groups, which are not intended to be limiting, include alkadiynes, alkatriynes, ethynyl, propynyl, butyryl, and the like.

In some embodiments, an aryl group is a univalent, substituted or unsubstituted, monocyclic or polycyclic aromatic hydrocarbon radical. In some embodiments, an aryl group is a radical which, in accordance with Hückel's theory, includes a cyclic, delocalized (4n+2) pi-electron system. In some embodiments the aryl group is a $C_5$-$C_{20}$ aryl group. The $C_5$-$C_{20}$ aryl group may suitably include $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ aryl groups. In some embodiments, the aryl group may be substituted or unsubstituted, be substituted with two or more groups that taken together form a cyclic group, or any combination thereof. In some embodiments, the aryl group is attached to the parent structure through one or more independent divalent intervening substituent groups. Some examples of aryl groups, which are not intended to be limiting, include phenyl, naphthyl, tetrahydronaphthyl, phenanthryl, pyrenyl, anthryl, indanyl, chrysyl, and the like.

In some embodiments, a heterocyclic group is a univalent, substituted or unsubstituted, saturated or unsaturated, mono- or polycyclic hydrocarbon radical that contains one or more heteroatoms in one or more of the rings. In some embodiments, the heterocyclic group is a $C_3$-$C_{20}$ cyclic group, in which one or more ring carbons is independently replaced with one or more heteroatoms. The $C_3$-$C_{20}$ heterocyclic group may suitably include $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ cyclic groups in which one or more ring carbons is independently replaced with one or more heteroatoms. In some embodiments, the heteroatoms are selected from one or more of N, O, or S, or any combination thereof. In some embodiments, the N or S or both may be independently substituted with one or more substituents. In some embodiments, the heterocyclic group is substituted or unsubstituted, saturated or unsaturated, mono-, bi-, tri-, or poly-cyclic, or any combination thereof. In some embodiments, one or more hydrogens may be optionally and independently replaced by one or more substituent groups. In some embodiments, the heterocyclic group may include one or more carbon-carbon double bonds, carbon-carbon triple bonds, carbon-nitrogen double bonds, or any combination thereof. In some embodiments, the heterocyclic group is attached to the parent structure through one or more independent divalent intervening substituent groups. Some examples of heterocyclic groups, which are not intended to be limiting, include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, 1,4-oxazin-2-yl, 1,2,5-oxathiazin-4-yl, and the like In some embodiments, a heteroaryl group is univalent, substituted or unsubstituted, monocyclic or polycyclic aromatic hydrocarbon radical in which one or more ring carbons is independently replaced with one or more heteroatoms selected from O, S and N. In some embodiments, in addition to said heteroatom, the heteroaryl group may optionally have up to 1, 2, 3, or 4 N atoms in the ring. In some embodiments, the heteroaryl group is an aryl group in which one or more ring carbons are independently replaced with one or more heteroatoms. In some embodiments, a heteroaryl group is an aromatic radical, which contains one or more heteroatoms and which, in accordance with Hückel's theory, includes a cyclic, delocalized (4n+2) pi-electron system. In some embodiments, the heteroaryl group is a $C_5$-$C_{20}$ heteroaryl group. The $C_5$-$C_{20}$ heteroaryl group may suitably include $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ aryl groups in which one or more than one ring carbon is independently replaced with one or more heteroatoms. In some embodiments, the heteroaryl group may be substituted or unsubstituted, be substituted with two or more groups that taken together form a cyclic group, or any combination thereof. In some embodiments, the heteroaryl group is attached to the parent structure through one or more independent divalent intervening substituent groups. Some examples of heteroaryl groups, which are not intended to be limiting, include heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like.

In some embodiments, an aralkyl group is a univalent radical derived from one or more aryl groups attached to one or more of an alkylene group, cycloalkylene group, alkenylene group, alkynylene group, or combination thereof. The alkylene, cycloalkylene, alkenylene, and alkynylene groups are divalent radicals derived from the removal of hydrogen from the respective alkyl, cycloalkyl, alkenyl, or alkynyl groups. In this context, any combination of aryl group and alkyl, cycloalkyl, alkenyl, or alkynyl group is contemplated. In some embodiments, the aryl group is attached to the parent structure through one or more of the alkylene group, cycloalkylene group, alkenylene group, alkynylene group, or combination thereof as appropriate. In some embodiments, the aralkyl group may be attached to the parent structure through one or more independent divalent intervening substituent groups.

In some embodiments, a heteroaralkyl group is a univalent radical derived from one or more heteroaryl groups attached to one or more of an alkylene group, cycloalkylene group, alkenylene group, alkynylene group, or combination thereof. The alkylene, cycloalkylene, alkenylene, and alkynylene groups are divalent radicals derived from the removal of hydrogen from the respective alkyl, cycloalkyl, alkenyl, or alkynyl groups. In this context, any combination of heteroaryl group and alkyl, cycloalkyl, alkenyl, or alkynyl group is contemplated. In some embodiments, the heteroaryl group is attached to the parent structure through one or more of the alkylene group, cycloalkylene group, alkenylene group, alkynylene group, or combination thereof as appropriate. In some embodiments, the heteroaralkyl group may be attached to the parent structure through one or more independent divalent intervening substituent groups.

In some embodiments, a halo group is a univalent halogen radical or halogen-containing substituent group, e.g., one that is or contains one or more F, Br, Cl, I, or combination thereof. As used herein, the term "halogen" or "halo" includes fluoro, chloro, bromo, or iodo, or fluoride, chloride, bromide or iodide. In some embodiments, a halogen containing substituent group may suitably include a substituent group in which one or more hydrogen atoms are independently replaced with one or more halogens. In some embodiments, the halo group may be attached to the parent structure through one or more independent divalent intervening substituent groups.

In some embodiments, a hydroxy group is a univalent hydroxyl radical (—OH) or hydroxy-containing substituent group, e.g., one that is or contains one or more —OH. As used herein the term, "hydroxy" includes an —OH group. In some embodiments, a hydroxy-containing substituent group may suitably include a substituent group in which one or more hydrogen atoms are independently replaced with one or more —OH groups. In some embodiments, the hydroxyl group may be attached to the parent structure through one or more independent divalent intervening substituent groups.

In some embodiments, an oxo group is a univalent radical that contains an oxygen atom, =O, doubly bonded to carbon or another element. In some embodiments, the oxo group suitably includes aldehydes, carboxylic acids, ketones, sulfonic acids, amides, esters, and combinations thereof. In some embodiments, the oxo group may be attached to the parent structure through one or more independent divalent intervening substituent groups.

In some embodiments, a mercapto or thiol group is a univalent —SR radical or an —SR— containing group. The R group is suitably chosen from any of the substituent groups. In some embodiments, the mercapto group may be attached to the parent structure through one or more independent divalent intervening substituent groups.

In some embodiments, an amino group is a univalent —NH$_2$ radical or an —NH$_2$-containing substituent group. In some embodiments, the amino group may be attached to the parent structure through one or more independent divalent intervening substituent groups.

In some embodiments, an alkylamino group is a univalent —NRH radical or an —NRH-containing substituent group. The R group is suitably chosen from any of the substituent groups. In some embodiments, the alkylamino group may be attached to the parent structure through one or more independent divalent intervening substituent groups.

In some embodiments, a dialkylamino group is a univalent —NRR radical or an —NRR-containing substituent group. The R groups may be the same or different and are suitably and independently chosen from any of the substituent groups. In some embodiments, the dialkylamino group may be attached to the parent structure through one or more independent divalent intervening substituent groups.

In some embodiments, an acyl or carbonyl group is a univalent radical that contains a —C(=O)R group. In some embodiments, the acyl group suitably includes aldehydes, ketones, and combinations thereof. The R group is suitably chosen from any of the substituent groups. In some embodiments, the carbonyl group may be attached to the parent structure through one or more independent divalent intervening substituent groups.

In some embodiments, a carboxylic acid group is a univalent —C(=O)OH radical or a —C(=O)OH-containing substituent group. In some embodiments, the carboxylic acid group may be attached to the parent structure through one or more independent divalent intervening substituent groups.

In some embodiments, a carboxylate group is a univalent —C(=O)O⁻ anion, —C(=O)OR, or —C(=O)OM, wherein M is a metal cation, or —C(=O)O⁻ anion, —C(=O)OR, or —C(=O)OM-containing substituent group. The R group is suitably chosen from any of the substituent groups. The metal cation is suitably chosen from Li, Na, K, and the like. In some embodiments, the carboxylate group may be attached to the parent structure through one or more independent divalent intervening substituent groups.

In some embodiments, an amidine group is a univalent —C(=NR)NRR radical or a —C(=NR)NRR-containing substituent group. The R groups may be the same or different and are suitably and independently chosen from any of the substituent groups. In some embodiments, the amidine group may be attached to the parent structure through one or more independent divalent intervening substituent groups.

In some embodiments, an amide group is a univalent -E(=O)NRR radical or a -E(=O)NRR-containing substituent group, in which E may be other than carbon, e.g., a chalcogen (e.g., S, Se, Te), or P. In some embodiments, the amide group suitably includes univalent lactams, peptides, phosphoramides, or sulfamides, —S(=O)$_2$NRR, —P(=O)(OH)NRR, and the like. The R groups may be the same or different and are suitably and independently chosen from any of the substituent groups. In some embodiments, the amide group may be attached to the parent structure through one or more independent divalent intervening substituent groups.

In some embodiments, a carbamoyl group is a univalent —C(=O)NRR radical or a —C(=O)NRR-containing substituent group. The R groups may be the same or different and are suitably and independently chosen from any of the substituent groups. In some embodiments, the carbamoyl group may be attached to the parent structure through one or more independent divalent intervening substituent groups.

In some embodiments, a sulfonyl group is a univalent —S(=O)$_2$R radical or a —S(=O)$_2$R-containing substituent group. The R group is suitably chosen from any of the substituent groups. In some embodiments, the sulfonyl group may be attached to the parent structure through one or more independent divalent intervening substituent groups.

In some embodiments, an alkylthio or sulfide group is a univalent —SR radical or an —SR-containing substituent group. The R group is suitably chosen from any of the substituent groups. In some embodiments, the alkylthio group may be attached to the parent structure through one or more independent divalent intervening substituent groups.

In some embodiments, an alkoxy group is a univalent radical derived from an —O-alkyl group. In some embodiments, the alkylthio group may be attached to the parent structure through one or more independent divalent intervening substituent groups.

In some embodiments, an aryloxy group is a univalent radical derived from an —O-aryl group. In some embodiments, the aryloxy group may be attached to the parent structure through one or more independent divalent intervening substituent groups.

In some embodiments, a heteroaryloxy group is a univalent radical derived from an —O-heteroaryl group. In some embodiments, the heteroaryloxy group may be attached to the parent structure through one or more independent divalent intervening substituent groups.

In some embodiments, an aralkoxy group is a univalent radical derived from an —O-aralkyl group. In some embodiments, the aralkoxy group may be attached to the parent structure through one or more independent divalent intervening substituent groups.

In some embodiments, a heteroaralkoxy group is a univalent radical derived from an —O-heteroaryl group. In some embodiments, the heteroaralkoxy group may be attached to the parent structure through one or more independent divalent intervening substituent groups.

In some embodiments, an alkylcarbonyl group is a univalent is radical derived from a -carbonyl-alkyl group. In some embodiments, the alkylcarbonyl group may be attached to the parent structure through one or more independent divalent intervening substituent groups.

In some embodiments, an alkoxycarbonyl group is a univalent radical derived from a -carbonyl-O-alkyl group. In some embodiments, the alkoxycarbonyl group may be attached to the parent structure through one or more independent divalent intervening substituent groups.

In some embodiments, an alkylaminocarbonyl group is a univalent radical derived from a -carbonyl-alkylamino group. In some embodiments, the heteroaralkoxy group may be attached to the parent structure through one or more independent divalent intervening substituent groups.

In some embodiments, a dialkylamino carbonyl group is a univalent radical derived from a -carbonyl-dialkylamino group. In some embodiments, the dialkylamino carbonyl group may be attached to the parent structure through one or more independent divalent intervening substituent groups.

In some embodiments, an arylcarbonyl group is a univalent radical derived from a -carbonyl-aryl group. In some embodiments, the arylcarbonyl group may be attached to the parent structure through one or more independent divalent intervening substituent groups.

In some embodiments, a heteroarylcarbonyl group is a univalent radical derived from a -carbonyl-heteroaryl group. In some embodiments, the heteroarylcarbonyl group may be attached to the parent structure through one or more independent divalent intervening substituent groups.

In some embodiments, an aryloxycarbonyl group is a univalent radical derived from a -carbonyl-O-aryl group. In some embodiments, the aryloxycarbonyl group may be attached to the parent structure through one or more independent divalent intervening substituent groups.

In some embodiments, an alkylsulfonyl group is a univalent radical derived from a -sulfonyl-alkyl group. In some embodiments, the alkylsulfonyl group may be attached to the parent structure through one or more independent divalent intervening substituent groups.

In some embodiments, an arylsulfonyl group is a univalent radical derived from a -sulfonyl-aryl group. In some embodiments, the arylsulfonyl group may be attached to the parent structure through one or more independent divalent intervening substituent groups.

In some embodiments, a perhaloalkyl group is a univalent radical derived from a completely or substantially completely halogenated alkyl group. In some embodiments, the parhaloalkyl group may be attached to the parent structure through one or more independent divalent intervening substituent groups.

In some embodiments, a perhaloalkoxy group is a univalent radical derived from a completely or substantially completely halogenated alkoxy group. In some embodiments, the arylsulfonyl group may be attached to the parent structure through one or more independent divalent intervening substituent groups.

In some embodiments, a perhalocycloalkyl group is a univalent radical derived from a completely or substantially completely halogenated cycloalkyl group. In some embodiments, the perhalocycloalkyl group may be attached to the parent structure through one or more independent divalent intervening substituent groups.

In some embodiments, a perhaloalkenyl group is a univalent radical derived from a completely or substantially completely halogenated alkenyl group. In some embodiments, the perhaloalkenyl group may be attached to the parent structure through one or more independent divalent intervening substituent groups.

In some embodiments, a perhaloalkynyl group is a univalent radical derived from a completely or substantially completely halogenated alkynyl group. In some embodiments, the perhaloalkynyl group may be attached to the parent structure through one or more independent divalent intervening substituent groups.

In some embodiments, a perhaloaryl group is a univalent radical derived from a completely or substantially completely halogenated aryl group. In some embodiments, the perhaloaryl group may be attached to the parent structure through one or more independent divalent intervening substituent groups.

In some embodiments, a perhaloaralkyl group is a univalent radical derived from a completely or substantially completely halogenated aralkyl group. In some embodiments, the perhaloaralkyl group may be attached to the parent structure through one or more independent divalent intervening substituent groups.

In some embodiments, referring to the replacement of one or more than one atom in each group with one or more heteroatoms, the heteroatoms may be suitably chosen from N, O, P, S, B, or any combination thereof.

The substituent groups are not particularly limiting. In some embodiments, the substituent group may be suitably and independently chosen from one or more of an acyl group, alkenyl group, alkoxy group, alkoxycarbonyl group, alkoxycarbonyloxy group, alkoxysulfonyloxy group, alkyl group, alkylamino group, alkylaminocarbonyl group, alkylcarbonyl group, alkylcarbonyloxy group, alkylsulfonyl group, alkylsulfonyloxy group, alkylthio group, alkynyl group, amide group, amidine group, amino group, aralkoxy group, aralkyl group, aryl group, arylcarbonyl group, arylcarbonyloxy group, aryloxy group, aryloxycarbonyl group, aryloxycarbonyloxy group, aryloxysulfonyloxy group, arylsulfonyl group, arylsulfonyloxy group, azido group, carbamido group, carbamoyl group, carbazoyl group, carbonyl group, carboxylate group, carboxylic acid group, cyanato group, cyano group, cycloalkenyl group, cycloalkyl group, dialkylamino carbonyl group, dialkylamino group, guanidino group, guanyl group, halo group, heteroaralkoxy group, heteroaralkyl group, heteroaryl group, heteroarylcarbonyl group, heteroaryloxy group, heterocyclic group, hydroxamino group, hydroxy group, imino group, isocyanato group, isocyano group, mercapto group, nitro group, oxo group, perhaloalkenyl group, perhaloalkoxy group, perhaloalkyl group, perhaloalkynyl group, perhaloaralkyl group, perhaloaryl group, perhalocycloalkyl group, phosphate group, phosphine group, phospho group, sulfate group, sulfo group, sulfonyl group, oxidized form thereof, or combination thereof. Oxidized forms of the groups are possible. In some embodiments, the substituent group may be optionally and independently directly connected to the relevant parent structure via one or more chemical bonds. In some embodiments, the substituent group may be optionally and independently indirectly connected to the relevant parent structure via one or more divalent intervening substituent groups. In some embodiments, the substituent group may be optionally and independently further substituted with one or more substituent group.

The divalent intervening substituent groups are not particularly limiting. In some embodiments, the divalent intervening substituent group may be suitably and independently chosen from one or more of an azo group, azino group, azoxy group, carbonyl group, dioyl group, diazoamino group, disulfinyl group, dithio group, oxy group, hydrazo group, oxalyl group, sulfonyl group, thiocarbonyl group, thionyl group, phosphono ester group, carboxylate group, thio group; divalent residue of one or more of the following groups: acyl group, alkenyl group, alkoxy group, alkoxycarbonyl group, alkoxycarbonyloxy group, alkoxysulfonyloxy group, alkyl group, alkylamino group, alkylaminocarbonyl group, alkylcarbonyl group, alkylcarbonyloxy group, alkylsulfonyl group, alkylsulfonyloxy group, alkylthio group, alkynyl group, amide group, amidine group, amino group, aralkoxy group, aralkyl group, aryl group, arylcarbonyl group, arylcarbonyloxy group, aryloxy group, aryloxycarbonyl group, aryloxycarbonyloxy group, aryloxysulfonyloxy group, arylsulfonyl group, arylsulfonyloxy group, azido group, carbamido group, carbamoyl group, carbazoyl group, carbonyl group, carboxylate group, carboxylic acid group, cyanato group, cyano group, cycloalkenyl group, cycloalkyl group, dialkylamino carbonyl group, dialkylamino group, guanidino group, guanyl group, heteroaralkoxy group, heteroaralkyl group, heteroaryl group, heteroarylcarbonyl group, heteroaryloxy group, heterocyclic group, hydroxamino group, hydroxy group, imino group, isocyanato group, isocyano group, mercapto group, nitro group, oxo group, perhaloalkenyl group, perhaloalkoxy group, perhaloalkyl group, perhaloalkynyl group, perhaloaralkyl group, perhaloaryl group, perhalocycloalkyl group, phosphate group, phosphine group, phospho group, sulfate group, sulfo group, sulfonyl group, oxidized form thereof, combination thereof; oxidized form thereof, or combination thereof. Oxidized forms of the groups are possible.

In some embodiments, the compound may be included in a mixture of diastereomers. If desired, the diastereomers can be separated by taking advantage of their different physical properties, such as using either recrystallization or chromatography or a combination thereof. The recrystallizations can accomplished in organic solvents such as, but not limited to, pentane, hexane, cyclohexane, toluene, benzene, chlorobutane, dichloromethane, diethyl ether, tetrahydrofuran, dimethoxyethane, acetonitrile, methanol, ethanol or butanol or a combination of organic solvents with or without water. The chromatography can be accomplished with a silica gel or alumina solid phase, eluting with mixtures of organic solvents, with or without acidic or basic modifiers, such as triethylamine, aqueous ammonia, acetic acid or aqueous hydrochloric acid.

In some embodiments, the compounds are suitable for the treatment and/or prevention of diseases and disorders characterized by mycobacterial activity or infection. The mycobacteria may be pathogenic or non-pathogenic. The mycobacteria may be Gram positive or Gram negative.

In some embodiments, the compound can be administered to a human patient by itself or in pharmaceutical compositions where it may be mixed with suitable carriers or excipients at doses to treat or ameliorate various conditions characterized by mycobacterial activity or infection. A therapeutically effective dose may refer to that amount of the compound sufficient to inhibit the mycobacterial activity or infection, it being understood that such inhibition may occur at different concentrations such that a person skilled in the art could determine the required dosage of compound to inhibit the target mycobacterial activity or infection. Therapeutically effective doses may be administered alone or as adjunctive therapy in combination with other treatments. Some examples of techniques for the formulation and administration of the compounds may be found in Remington's Pharmaceutical Sciences, 18th Edition, A. R. Gennaro, Ed., Mack Publishing Co., Easton, Pa. (1990).

Suitable routes of administration may, for example, include oral, rectal, transmucosal, buccal, intravaginal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation. Furthermore, one may administer the compound in a targeted drug delivery system, for example in a liposome.

The pharmaceutical compositions and compounds may be manufactured in a manner that is itself known, e.g., by means of conventional mixing, dissolving, dragee-making, levitating, emulsifying, encapsulating, entrapping, or lyophilizing processes. The pharmaceutical compositions thus may be formulated in conventional manner using one or more physiologically acceptable carriers comprising excipients and auxiliaries that facilitate processing of the active compounds into preparations, which can be used pharmaceutically. Proper formulation may be dependent upon the route of administration chosen.

Any combination of one or more the present compounds, salts thereof, resonance forms thereof, prodrugs, metabolites, isotopically-labeled compounds, tautomers, isomers, and/or atropisomers is possible in the composition.

For injection, the compounds may be formulated in aqueous solutions, preferably in physiologically compatible buffers, such as Hank's solution, Ringer's solution, or physiological saline buffer. For transmucosal administration, penetrants appropriate to the barrier to be permeated are used in the formulation. Such penetrants are known in the art.

For oral administration, the compounds can be formulated readily by combining the active compounds with pharmaceutically acceptable carriers well known to those in the art. Such carriers enable the compounds to be formulated as tablets, pills, dragees, capsules, liquids, gels, syrups, slurries, suspensions and the like, for oral ingestion by a patient to be treated. Pharmaceutical preparations for oral use can be obtained by combining the compound with a solid excipient, optionally grinding the resulting mixture, and processing the mixture of granules, after adding suitable auxiliaries, if desired, to obtain tablets or dragee cores. Suitable excipients include but are not limited to fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as polyionic block (co)polymer, sodium carboxymethyl cellulose, sorbitol, or dextran. Optionally, the suspension may also contain suitable stabilizers or agents which increase the solubility of the compounds.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

The compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid- or gel-phase carriers or excipients. Examples of such carriers or excipients include but are not limited to calcium carbonate, calcium phosphate, various sugars, starches, cellulose derivatives, gelatin, and polymers such as polyethylene glycols.

In some embodiments, the compounds may be provided as salts with pharmaceutically compatible counterions. Pharmaceutically compatible salts may be formed with many acids, including but not limited to hydrochloric, sulfuric, acetic, lactic, tartaric, malic, succinic, etc.; or bases. Non-limiting examples of pharmaceutically acceptable salts include sodium, potassium, lithium, calcium, magnesium, iron, zinc, hydrochloride, hydrobromide, hydroiodide, acetate, citrate, tartrate and maleate salts, and the like.

Generally, pharmaceutical compositions contain the active compound in an effective amount to achieve their intended purpose. In one embodiment, a therapeutically effective amount means an amount effective to prevent or inhibit development or progression of a disease characterized by mycobacterial infection or activity in the subject being treated. Determination of the effective amounts is within the capability of those skilled in the art in light of the description provided herein.

Any group described herein, whether it is expressly denoted as a "group" or is not denoted as such (e.g., using terms such as "alkyl," "aryl," "aroyl," and the like, alone) may be optionally and independently straight or branched; may be optionally and independently substituted by one or more independent substituent groups; may be optionally and independently attached directly to the relevant parent structure; may be optionally and independently attached indirectly to the relevant parent structure via one or more divalent intervening substituent groups; and/or may have one or more than one atom optionally and independently replaced with one or more independent heteroatoms.

The use of the word "a" or "an" when used in conjunction with the term "comprising" in the claims and/or the specification may mean "one," but it is also consistent with the meaning of "one or more," "at least one," and "one or more than one."

The term, "about" is used to indicate that a value includes the standard deviation of error.

The term, "or" means "and/or" unless explicitly indicated to refer to alternatives only or the alternatives are mutually exclusive, although the disclosure supports a definition that refers to only alternatives and "and/or."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The design and syntheses of 1,3-benzothiazinone azide (BTZ-N3) and related Click chemistry products based on the molecular mode of activation of BTZ043 are described. The inventors' computational docking studies indicate that BTZ-N3 binds in the essentially same pocket as that of BTZ043; however their model biochemical reactivity studies with nucleophiles such as thiolates and cyanide indicate that, in contrast to BTZ043, the azide analog is an ambident electrophile. Consequently, it is believed that the mode of activation and/or inactivation of DprE1 by BTZ-N3 could involve alternative mechanisms. The in vitro activity of BTZ-N3 further substantiates the docking studies and as it demonstrates impressive activity against the H37Rv strain of Mtb. On the other hand, the products obtained from click reactions of BTZ-N3 with representative alkynes show much weaker activity. These and other results herein highlight the importance of electron withdrawing character of the aromatic ring in the benzothiazinone class of anti-TB agents.

Other embodiments of the invention are discussed throughout this application. Any embodiment discussed with respect to one aspect applies to other embodiments as well and vice versa. Each embodiment described herein and any obvious variation thereof is understood to be applicable to all embodiments of the invention. Given the description herein, combined with the knowledge of one of ordinary skill in the art to which the invention pertains, any embodiment described herein can be easily accomplished and/or further implemented with respect to any use, method, compound, composition, kit, obvious variant thereof, or any combination thereof.

Abbreviations: DMF, N,N-dimethyl formamide; DprE1, decaprenylphosphoryl-β-D-ribose 2' oxidase; MDR, multi-drug resistant; *M. tuberculosis, Mycobacterium tuberculosis*; XDR, extensively drug resistant; TB, tuberculosis.

What is claimed is:

1. A compound, having the following formula:

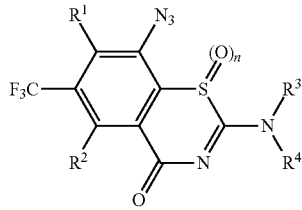

(I)

or resonance form thereof, or salt thereof, or salt of resonance form thereof;
wherein $R^1$-$R^4$ are each independently hydrogen, an alkyl group, a cycloalkyl group, a cycloalkenyl group, a halo group, an alkenyl group, an alkynyl group, an aryl group, a hydroxy group, an acyl group, an oxo group, a mercapto group, an alkylthio group, an alkoxy group, a heterocyclic group, a heteroaryl group, a heteroarylcarbonyl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an alkylsulfonyl group, an arylsulfonyl group, perhaloalkyl group, a perhaloalkoxy group, a perhalocycloalkyl group, a perhaloalkenyl group, a perhaloalkynyl group, a perhaloaryl group, a perhaloaralkyl group, or combination thereof;
wherein $R^3$ and $R^4$ may be taken together with the nitrogen to which they are attached to form a substituted or unsubstituted, saturated or unsaturated, mono-, bi-, tri-, or polycyclic heterocyclic group;
wherein each group may be optionally and independently straight, branched substituted, or unsubstituted; and wherein one or more than one atom in each group may be optionally and independently replaced with one or more independent heteroatoms;
wherein n is 0, 1, or 2.

2. The compound of claim 1, wherein $R^1$-$R^4$ are each independently hydrogen, alkyl, allyl, cycloalkyl, aryl, acyl, aroyl, or combination thereof,
said alkyl and allyl being independently linear, branched, substituted, unsubstituted, or combination thereof,
said cycloalkyl being substituted or unsubstituted, the alkyl portion of which being linear, branched, substituted, unsubstituted, or combination thereof,
said aryl, acyl, and aroyl being independently substituted or unsubstituted;
and wherein $R^3$ and $R^4$ taken together with the nitrogen to which they are attached may optionally form a heterocyclic group, said heterocyclic group being substituted, unsubstituted, saturated, unsaturated, or combination thereof.

3. The compound of claim 1, wherein one or more than one atom in one or more of $R^1$-$R^4$ is independently replaced with one or more independent heteroatom.

4. The compound of claim 1, wherein one or more than one carbon in one or more of $R^1$-$R^4$ is independently replaced with one or more independent heteroatom selected from the group consisting of N, O, S, or combination thereof.

5. The compound of claim 1, wherein $R^1$-$R^4$ are independently hydrogen, alkyl, substituted alkyl, linear alkyl, branched alkyl, allyl, substituted allyl, heteroalkyl, cycloalkyl, aryl, substituted aryl, heteroaryl, acyl, aroyl, heteroaroyl, or combination thereof.

6. The compound of claim 1, wherein $R^3$ and $R^4$ taken together with the nitrogen to which they are attached form a $C_3$-$C_{10}$ heterocyclic group, said heterocyclic group being substituted, unsubstituted, saturated, unsaturated, or combination thereof.

7. The compound of claim 1 wherein $R^3$ and $R^4$ taken together with the nitrogen to which they are attached form a $C_3$-$C_6$ heterocyclic group.

8. The compound of claim 1, having one of the following formulas:

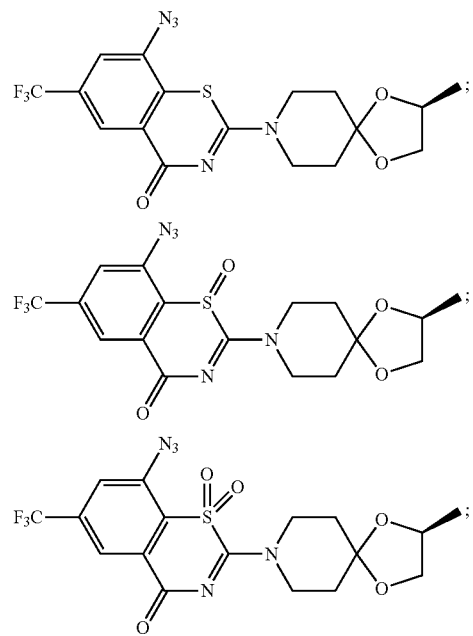

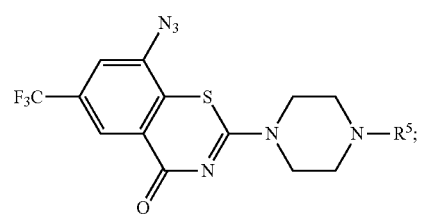

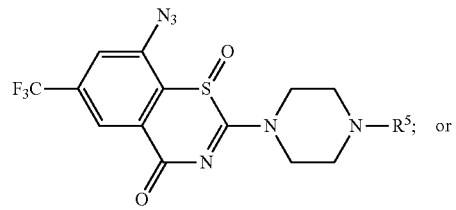

-continued

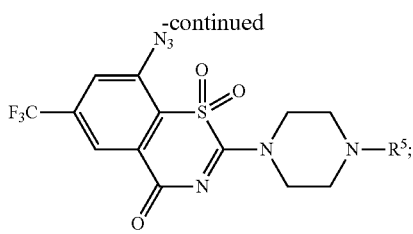

wherein R⁵ is hydrogen, an alkyl group, a cycloalkyl group, a cycloalkenyl group, a halo group, an alkenyl group, an alkynyl group, an aryl group, a hydroxy group, an acyl group, an oxo group, a mercapto group, an alkylthio group, an alkoxy group, a heterocyclic group, a heteroaryl group, a heteroarylcarbonyl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an alkylsulfonyl group, an arylsulfonyl group, perhaloalkyl group, a perhaloalkoxy group, a perhalocycloalkyl group, a perhaloalkenyl group, a perhaloalkynyl group, a perhaloaryl group, a perhaloaralkyl group, or combination thereof; and wherein each group may be optionally and independently straight, branched substituted, or unsubstituted; and wherein one or more than one atom in each group may be optionally and independently replaced with one or more independent heteroatoms.

9. A pharmaceutical composition, comprising the compound of claim 1 and a physiologically acceptable carrier.

10. A method of treating a subject known or suspected to need treatment for one or more maladies related to non-pathogenic mycobacterial strain, *M. smegmatis, M. vaccae, M. aurum*, Gram positive bacteria, *S. aureus, M. luteus*, Gram negative bacteria, *P. aeruginosa, A. baumanii*, pathogenic mycobacterial strain, *M. tuberculosis, M. bovis, M. marinum, M. kansasaii*, H37Rv, *M. africanum, M. canetti, M. caprae, M. microti, M. mungi, M. pinnipedii*, myobacterium tuberculosis complex, tuberculosis, or combination thereof, comprising administering the compound of claim 1 to said subject, to treat said subject.

11. A method of treating a subject known or suspected to need treatment for one or more maladies related to non-pathogenic mycobacterial strain, *M. smegmatis, M. vaccae, M. aurum*, Gram positive bacteria, *S. aureus, M. luteus*, Gram negative bacteria, *P. aeruginosa, A. baumanii*, pathogenic mycobacterial strain, *M. tuberculosis, M. bovis, M. marinum, M. kansasaii*, H37Rv, *M. africanum, M. canetti, M. caprae, M. microti, M. mungi, M. pinnipedii*, myobacterium tuberculosis complex, tuberculosis, or combination thereof, comprising administering the composition of claim 9 to said subject, to treat said subject.

12. The compound of claim 1, wherein $R^1$ and $R^2$ are hydrogen.

13. The compound of claim 1, wherein n=0.

14. The compound of claim 1, wherein n=1.

15. The compound of claim 1, wherein n=2.

16. The compound of claim 1, wherein in the group:

$R^3$ and $R^4$ are taken together to form a heterocyclic group having the following cyclic structure (II):

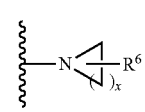

(II)

wherein x is 1-10, and $R^6$ is hydrogen, an alkyl group, a cycloalkyl group, a cycloalkenyl group, an alkenyl group, an alkynyl group, an aryl group, a heterocyclic group, a heteroaryl group, an aralkyl group, a heteroaralkyl group, oxidized form thereof, or combination thereof.

17. The compound of claim 1, wherein $R^3$ and $R^4$ taken together with the nitrogen to which they are attached form a substituted or unsubstituted, saturated or unsaturated, mono-, bi-, tri-, or polycyclic heterocyclic group.

18. The compound of claim 1, wherein $R^3$ and $R^4$ taken together with the nitrogen to which they are attached form a substituted or unsubstituted, saturated or unsaturated, mono- bi-, tri-, or polycyclic $C_3$-$C_{20}$ heterocyclic group.

19. The compound of claim 1, wherein $R^3$ and $R^4$ taken together with the nitrogen to which they are attached form a azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, 1,4-oxazin-2-yl, or 1,2,5-oxathiazin-4-yl group.

20. The compound of claim 1, wherein in the group:

$R^3$ and $R^4$ are taken together to form a heterocyclic group having one of the following structures:

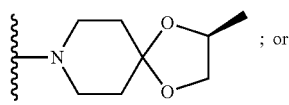

; or

-continued

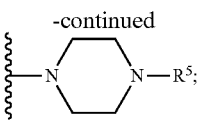

wherein $R^5$ is hydrogen, an alkyl group, a cycloalkyl group, a cycloalkenyl group, a halo group, an alkenyl group, an alkynyl group, an aryl group, a hydroxy group, an acyl group, an oxo group, a mercapto group, an alkylthio group, an alkoxy group, a heterocyclic group, a heteroaryl group, a heteroarylcarbonyl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an alkylsulfonyl group, an arylsulfonyl group, perhaloalkyl group, a perhaloalkoxy group, a perhalocycloalkyl group, a perhaloalkenyl group, a perhaloalkynyl group, a perhaloaryl group, a perhaloaralkyl group, or combination thereof; and wherein each group may be optionally and independently straight, branched substituted, or unsubstituted; and wherein one or more than one atom in each group may be optionally and independently replaced with one or more independent heteroatoms.

\* \* \* \* \*